United States Patent
MacDonald et al.

(10) Patent No.: US 8,535,617 B2
(45) Date of Patent: Sep. 17, 2013

(54) BLOOD CELL BARRIER FOR A LATERAL FLOW DEVICE

(75) Inventors: J. Gavin MacDonald, Decatur, GA (US); Molly K. Smith, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1077 days.

(21) Appl. No.: 11/948,127

(22) Filed: Nov. 30, 2007

(65) Prior Publication Data

US 2009/0142229 A1   Jun. 4, 2009

(51) Int. Cl.
*G01N 21/77*   (2006.01)

(52) U.S. Cl.
USPC .......... 422/420; 422/421; 422/422; 422/423; 422/424; 422/425

(58) Field of Classification Search
None
See application file for complete search history.

(56) References Cited

U.S. PATENT DOCUMENTS

| | | | |
|---|---|---|---|
| 3,552,928 A | 1/1971 | Fetter | |
| 3,700,623 A | 10/1972 | Keim | |
| 3,772,076 A | 11/1973 | Keim | |
| 3,962,436 A * | 6/1976 | Nakamura et al. | 514/162 |
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquist et al. | |
| 4,477,575 A | 10/1984 | Vogel et al. | |
| 4,537,657 A | 8/1985 | Keim | |
| 4,614,723 A | 9/1986 | Schmidt et al. | |
| 4,810,470 A | 3/1989 | Burkhardt et al. | |
| 4,987,085 A | 1/1991 | Allen et al. | |

(Continued)

FOREIGN PATENT DOCUMENTS

| | | |
|---|---|---|
| DE | 10222979 A1 | 12/2003 |
| EP | 0566046 A1 | 10/1993 |

(Continued)

OTHER PUBLICATIONS

Haurowitz (Journal of Biological Chemistry Apr. 23, 1941 pp. 353-359).*

(Continued)

*Primary Examiner* — Sally Merkling
(74) *Attorney, Agent, or Firm* — Dority & Manning, P.A.

(57) ABSTRACT

A lateral flow device for analyzing a whole blood sample is provided. More specifically, the lateral flow device contains a porous membrane that defines a barrier zone for separating red blood cells from blood plasma (includes plasma in which clotting factors haven been removed), which may then flow to a subsequent detection zone for analysis. The barrier zone is formed from a blood cell barrier composition that includes an unsaturated aliphatic fatty acid or an ester thereof. Without intending to be limited by theory, the present inventors believe such unsaturated aliphatic fatty acid molecules undergo autoxidation in the presence of air and hemoglobin to release peroxides (e.g., hydrogen peroxide) via oxidative saturation of double bonds. In turn, the released peroxides are believed to induce the formation of echinocytes or crenated blood cells. The crenated red blood cells are distorted in shape and less flexible and malleable than normal red blood cells, making them less able to penetrate into the pores of the porous membrane of the lateral flow device. Consequently, the stiffer, less flexible cells cannot move easily into the porous and become trapped at the surface of the membrane, while the liquid components of the sample flow and penetrate through the membrane to the detection zone for analysis.

23 Claims, 1 Drawing Sheet

(56) References Cited

U.S. PATENT DOCUMENTS

| | | | |
|---|---|---|---|
| 5,075,077 A | 12/1991 | Durley, III et al. | |
| 5,166,051 A * | 11/1992 | Killeen et al. | 435/7.1 |
| 5,208,535 A | 5/1993 | Nakayama et al. | |
| 5,234,813 A | 8/1993 | McGeehan et al. | |
| 5,252,459 A | 10/1993 | Tarcha et al. | |
| 5,306,623 A | 4/1994 | Kiser et al. | |
| 5,395,754 A | 3/1995 | Lambotte et al. | |
| 5,416,000 A | 5/1995 | Allen et al. | |
| 5,418,142 A * | 5/1995 | Kiser et al. | 435/14 |
| 5,464,741 A | 11/1995 | Hendrix | |
| 5,518,883 A | 5/1996 | Soini | |
| 5,527,892 A | 6/1996 | Borsotti et al. | |
| 5,558,834 A | 9/1996 | Chu et al. | |
| 5,573,909 A | 11/1996 | Singer et al. | |
| 5,585,279 A | 12/1996 | Davidson | |
| 5,589,399 A | 12/1996 | Allen et al. | |
| 5,591,581 A | 1/1997 | Massey et al. | |
| 5,637,509 A | 6/1997 | Hemmilä et al. | |
| 5,670,381 A | 9/1997 | Jou et al. | |
| 5,725,774 A | 3/1998 | Neyer | |
| 5,731,147 A | 3/1998 | Bard et al. | |
| 5,753,497 A | 5/1998 | Bernstein et al. | |
| 5,770,543 A | 6/1998 | Garst et al. | |
| 5,798,272 A | 8/1998 | Allen et al. | |
| 5,922,537 A | 7/1999 | Ewart et al. | |
| 5,939,331 A | 8/1999 | Burd et al. | |
| 5,981,294 A | 11/1999 | Blatt et al. | |
| 6,004,530 A | 12/1999 | Sagner et al. | |
| 6,008,059 A | 12/1999 | Schrier et al. | |
| 6,030,840 A | 2/2000 | Mullinax et al. | |
| 6,194,220 B1 | 2/2001 | Malick et al. | |
| 6,242,268 B1 | 6/2001 | Wieder et al. | |
| 6,261,779 B1 | 7/2001 | Barbera-Guillem et al. | |
| 6,362,011 B1 | 3/2002 | Massey et al. | |
| 6,365,417 B1 | 4/2002 | Fleming et al. | |
| 6,436,651 B1 | 8/2002 | Everhart et al. | |
| 6,444,423 B1 | 9/2002 | Meade et al. | |
| 6,468,741 B1 | 10/2002 | Massey et al. | |
| 6,582,930 B1 | 6/2003 | Ponomarev et al. | |
| 6,585,939 B1 | 7/2003 | Dapprich | |
| 6,613,583 B1 | 9/2003 | Richter et al. | |
| 7,001,715 B2 | 2/2006 | Houtchens et al. | |
| 7,083,939 B2 | 8/2006 | Shull et al. | |
| 7,271,008 B2 * | 9/2007 | Floyd | 436/518 |
| 2002/0036170 A1 | 3/2002 | Harvey et al. | |
| 2002/0081575 A1 | 6/2002 | Small et al. | |
| 2003/0031592 A1 * | 2/2003 | Knappe | 422/56 |
| 2003/0032196 A1 | 2/2003 | Zhou | |
| 2003/0113528 A1 | 6/2003 | Moya | |
| 2003/0118480 A1 | 6/2003 | Kaylor et al. | |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2003/0139886 A1 | 7/2003 | Bodzin et al. | |
| 2003/0149348 A1 | 8/2003 | Raskas | |
| 2004/0043507 A1 | 3/2004 | Song et al. | |
| 2004/0043511 A1 | 3/2004 | Song et al. | |
| 2004/0082077 A1 | 4/2004 | Hu | |
| 2004/0087034 A1 | 5/2004 | Lien | |
| 2004/0106190 A1 | 6/2004 | Yang et al. | |
| 2004/0121334 A1 | 6/2004 | Wei et al. | |
| 2004/0126833 A1 | 7/2004 | Shull et al. | |
| 2005/0011759 A1 | 1/2005 | Moerman et al. | |
| 2005/0084982 A1 | 4/2005 | Brauner | |
| 2005/0112780 A1 | 5/2005 | Song | |
| 2005/0136500 A1 | 6/2005 | Yang et al. | |
| 2006/0246597 A1 | 11/2006 | Feaster et al. | |
| 2006/0246600 A1 | 11/2006 | Yang et al. | |
| 2007/0048807 A1 | 3/2007 | Song | |

FOREIGN PATENT DOCUMENTS

| | | |
|---|---|---|
| EP | 0883159 A2 | 4/1998 |
| GB | 2090659 A | 7/1982 |
| WO | WO 9723780 A | 7/1997 |
| WO | WO 0050891 A1 | 8/2000 |
| WO | WO 0063697 A1 | 10/2000 |
| WO | WO 0078917 A1 | 12/2000 |
| WO | WO 0117797 A1 | 3/2001 |
| WO | WO 0198785 A2 | 12/2001 |
| WO | WO 0198785 A3 | 12/2001 |
| WO | WO 03000897 A2 | 1/2003 |
| WO | WO 03000897 A3 | 1/2003 |
| WO | WO 03002557 A1 | 3/2003 |
| WO | WO 03058246 A1 | 7/2003 |
| WO | WO 2005117556 A2 | 12/2005 |
| WO | WO 2005117556 A3 | 12/2005 |
| WO | WO 2007027198 A1 | 3/2007 |

OTHER PUBLICATIONS

Search Report and Written Opinion for PCT/IB2008/053708 dated Apr. 29, 2009.
Article—*Flow-Based Microimmunoassay*, Hayes et al., Anal. Chem., vol. 93, No. 24, Dec. 15, 2001, pp. 5896-5902.
Report by David L. Carlberg entitled *High-volume Manufacturing of Lateral Flow Assays*, 3 pages.
Data Sheet for MF-Millipore™ Filters from Millipore, 5 pages, retrieved from www.millipore.com.
Product Catalogue—MF-Millipore™ Membrane Filters, 6 pages, retrieved from www.wolff-cellulosics.de.
Product Information Sheet—Nitrocellulose in Solution from Wolff Cellulosics, 4 pages.
Article—Nakamura et al., "Effect of Hemoglobin Concentration on the Oxidation of Linoleic Acid," *Journal of Lipid Research*, vol. 12., 1971: p. 149-154.
Article—Yin et al. "Direct Electrochemistry of Hemoglobin Immobilized on Gold Electrode by Langmuir-Blodgett Technique," *Biosensors and Bioelectronics*, vol. 21, Issue 1, Jul. 2005: p. 21-29.
Article—Haurowitz et al, "Destruction of Hemin and Hemoglobin by the Action of Unsaturated Fatty Acids and Oxygen," *The Journal of Biological Chemistry*, Apr. 23, 1941: p. 353-359.
Article—Enoch Kim et al., "Solvent-Assisted Microcontact Molding: A Convenient Method for Fabricating Three-Dimentional Structures on Surfaces of Polymers," *Advanced Materials*, vol. 9, No. 8, Jun. 1997: pp. 651-654.
Article—Takeo Kawase et al., "Inkjet Printed Via-Hole Interconnections and Resistors for All-Polymer Transistor Circuits," *Advanced Materials*, vol. 13, No. 21, Nov. 2, 2001: pp. 1601-1605.

* cited by examiner

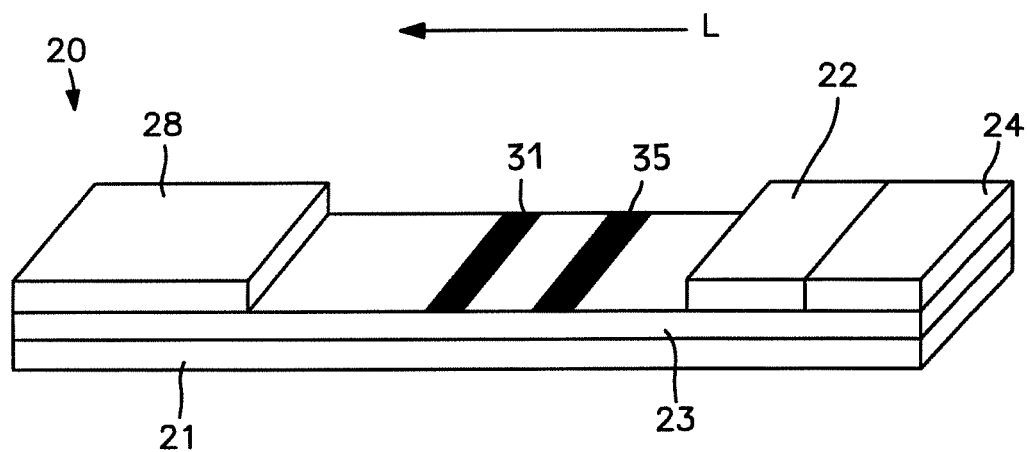

BLOOD CELL BARRIER FOR A LATERAL FLOW DEVICE

BACKGROUND OF THE INVENTION

Most clinical assays for analytes in blood begin with a blood plasma separation step to prevent red blood cells from interfering with the test procedure. Red blood cells typically constitute about half of the volume of a blood sample. Unless the red blood cells are substantially removed, their presence can affect clinical assay results that are sensitive to color. Whole blood also can interfere chemically. For example, hemoglobin that is released from red blood cells can affect the performance of certain clinical assays by virtue of the iron heme group, which can act as a catalyst in some chemical reactions. The conventional manner of separating plasma from red blood cells is by centrifugation. However, recent advances in clinical test methods has led to the development of rapid test devices that can be used by untrained individuals outside of a laboratory setting. Centrifugation is not practical for use in these procedures. Consequently, an effort has been made to develop simple red blood cell separators that do not require expensive or labor intensive instrumentation. Early attempts to remove red blood cell interferences within a test strip have focused on simple assay devices that do not require a wash or separation step. An example of one such attempt is U.S. Pat. No. 4,477,575, which describes a blood filter made from glass fiber that can separate out red blood cells when whole blood is slowly trickled onto one side. This blood filter was incorporated into a clinical assay test by physically affixing it to a reagent pad that contained reagents to and which produced a color in the presence of cholesterol.

The use of membranes to separate plasma from red blood cells has been known for many years. One attempt to improve on this conventional procedure is described in U.S. Pat. No. 5,166,051. This patent describes hardening red blood cells by treating them with a salt-based crenating agent (e.g., potassium chloride). Unfortunately, such crenating agents often affect chemical reactions. Furthermore, the red blood cell separator of this patent is not readily adapted for use in a rapid and sensitive sandwich-type immunoassay test strip.

As such, a need currently exists for an improved technique of separating red blood cells from a whole blood sample in a lateral flow assay device.

SUMMARY OF THE INVENTION

In accordance with one embodiment of the present invention, a lateral flow device for detecting the presence of an analyte in a whole blood sample is disclosed. The device comprises a barrier zone for separating red blood cells from the whole blood sample and a detection zone for detecting the analyte. The detection zone is located downstream from the barrier zone and in fluid communication therewith. Further, the barrier zone is formed from a blood cell barrier composition that comprises an unsaturated aliphatic acid or ester thereof having a carbon chain of at least $C_8$ and more than one carbon-carbon double bond.

In accordance with another embodiment of the present invention, a method for detecting the presence of an analyte in a whole blood sample is disclosed. The method comprises providing a lateral flow device that comprises a barrier zone and a detection zone in fluid communication therewith, wherein the barrier zone is formed from a blood cell barrier composition that comprises an unsaturated aliphatic acid or ester thereof having a carbon chain of at least $C_8$ and more than one carbon-carbon double bond. The barrier zone is contacted with the whole blood sample so that red blood cells are separated from blood plasma. The blood plasma flows to the detection zone and presence of the analyte is detected within the detection zone.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGURE in which:

FIG. 1 is a schematic illustration of one embodiment of a lateral flow assay device that may be employed in the present invention.

Repeat use of references characters in the present specification and drawing is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryonic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and 4,366,241 to Tom et al.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a lateral flow device for analyzing a whole blood sample. More specifically, the lateral flow device contains a porous membrane that defines a barrier zone for separating red blood cells from blood plasma (includes plasma in which clotting factors haven been removed), which may then flow to a subsequent detection zone for analysis. The barrier zone is particularly effective for blood samples having a relatively low volume, such as less than about 100 microliters, in some embodiments less than about 25 microliters, and in some embodiments, less than about 10 microliters. For example, whole blood drops obtained from patients with a lancet from low-pain areas (due to reduced nerve endings than finger), such as the forearm, thigh, or other alternate sites, may have a volume of from about 0.1 to about 5 microliters.

The barrier zone is formed from a blood cell barrier composition that includes an unsaturated aliphatic fatty acid or an ester thereof. Without intending to be limited by theory, the present inventors believe such unsaturated aliphatic fatty acid molecules undergo autoxidation in the presence of air and hemoglobin to release peroxides (e.g., hydrogen peroxide) via oxidative saturation of double bonds. In turn, the released peroxides are believed to induce the formation of echinocytes or "crenated" blood cells. Crenation is the contraction or formation of abnormal notchings around the edges of a cell after exposure to a hypertonic solution, which causes a net movement of water out of the cell through osmosis and thus a decrease in the volume of the cell cytoplasm. The crenated red blood cells are distorted in shape and less flexible and malleable than normal red blood cells, making them less able to penetrate into the pores of the porous membrane of the lateral flow device. Consequently, the stiffer, less flexible cells cannot move easily into the porous and become trapped at the surface of the membrane, while the liquid components of the sample flow and penetrate through the membrane to the detection zone for analysis.

The unsaturated aliphatic fatty acid (or ester of) of the blood cell barrier composition has a carbon chain of at least $C_8$, in some embodiments at least $C_{10}$, in some embodiments at least $C_{15}$, and in some embodiments, $C_{18}$-$C_{26}$. The aliphatic acid or ester also typically has more than one carbon-carbon double bond, such as at least 2, in some embodiments at least 3, and in some embodiments, at least 4. Table 1 lists various suitable unsaturated fatty acids that may be employed arranged in three groups: omega-6, omega-3, and omega-9, wherein the term "omega" signifies where the first double bond in the carbon backbone of the fatty acid occurs. Omega-6 signifies, for instance, that the first double bond occurs at the sixth carbon from the end of the fatty acid (i.e., the omega minus 6 position).

TABLE 1

| Common Name | Lipid Name | Chemical Name |
|---|---|---|
| Omega-6 fatty acids | | |
| Linoleic acid | 18:2 (n-6) | 9,12-octadecadienoic acid |
| γ-linolenic acid | 18:3 (n-6) | 6,9,12-octadecatrienoic acid |
| Eicosadienoic acid | 20:2 (n-6) | 11,14-eicosadienoic acid |
| Dihomo-γ-linolenic acid | 20:3 (n-6) | 8,11,14-eicosatrienoic acid |
| Arachidonic acid | 20:4 (n-6) | 5,8,11,14-eicosatetraenoic acid |
| Docosadienoic acid | 22:2 (n-6) | 13,16-docosadienoic acid |
| Adrenic acid | 22:4 (n-6) | 7,10,13,16-docosatetraenoic acid |
| Docosapentaenoic acid | 22:5 (n-6) | 4,7,10,13,16-docosapentaenoic acid]] |
| Calendic acid | 18:3 (n-6) | 8E,10E,12Z-octadecatrienoic acid |
| Omega-3 fatty acids | | |
| α-Linolenic acid (ALA) | 18:3 (n-3) | octadeca-9,12,15-trienoic acid |
| Stearidonic acid | 18:4 (n-3) | octadeca-6,9,12,15-tetraenoic acid |
| Eicosatetraenoic acid | 20:4 (n-3) | eicosa-8,11,14,17-tetraenoic acid |
| Eicosapentaenoic acid (EPA) | 20:5 (n-3) | eicosa-5,8,11,14,17-pentaenoic acid |
| Docosapentaenoic acid | 22:5 (n-3) | docosa-7,10,13,16,19-pentaenoic acid |
| Docosahexaenoic acid (DHA) | 22:6 (n-3) | docosa-4,7,10,13,16,19-hexaenoic acid |
| Omega-9 fatty acids | | |
| oleic acid | 18:1 (n-9) | 9-octadecenoic acid |
| eicosenoic acid | 20:1 (n-9) | 11-eicosenoic acid |
| mead acid | 20:3 (n-9) | 5,8,11-eicosatrienoic acid |
| erucic acid | 22:1 (n-9) | 13-docosenoic acid |
| nervonic acid | 24:1 (n-9) | 15-tetracosenoic acid |

The omega-3 and -6 fatty acids tend to function best in separating red blood cells as they generally contain a large numbers of unsaturated bonds. Particularly suitable unsaturated fatty acids are linoleic acid ($CH_3(CH_2)_4$ $CH$=$CHCH_2CH$=$CH(CH_2)_7COOH$); α-linoleic acid ($CH_3CH_2CH$=$CHCH_2CH$=$CHCH_2CH$=$CH(CH_2)_7$ $COOH$); arachidonic acid ($CH_3(CH_2)_4$ $CH$=$CHCH_2CH$=$CHCH_2CH$=$CHCH_2CH$=$CH(CH_2)_3$ $COOH$); eicosapentaenoic acid ($CH_3(CH_2CH$=$CH)_5(CH_2)_3$ $COOH$); docosahexaenoic acid ($CH_3(CH_2CH$=$CH)_6$ $CH_2CH_2COOH$); eicosadienoinc acid, eicosatrienoic acid ($CH_3(CH_2)_3(CH_2CH$=$CH)_3(CH_2)_6COOH$); etc. Still other suitable fatty acids may be described in U.S. patent application Ser. No. 11/801,612, filed on May 10, 2007, which is incorporated herein in its entirety by reference thereto for all purposes.

Many unsaturated aliphatic acids are also present as a glyceride component of natural-occurring seed oils, such as safflower, grape or pumpkin or soybean, or linseed, or peanut, or poppy, or perilla or a mixture thereof. These fatty acids can be easily and inexpensively extracted from these common seeds. For example, linoleic acid is stored usually in the form of glycerol and found in the seeds of certain plants, such as grapes, flax, safflowers, and peanuts, and fish. The highest levels of linoleic acid are in safflower (carthame) seeds (68-80%), grape seeds (65-73%), and pumpkin seed oil (45-60%). Table 2, provides a list of some examples of natural seed oils and their linoleic and linolenic acid content, respectively, which may be employed in the barrier zone of the present invention.

TABLE 2

| Seed | Linolenic Acid % Total Oil | Linoleic Acid % Total Oil |
|---|---|---|
| Almond | 0 | 17 |
| Avocado | 0 | 10 |
| Beech | 0 | 32 |
| Brazil | 0 | 24 |
| Cashew | 0 | 6 |
| Chia | 30 | 40 |
| Coconut | 0 | 3 |
| Corn | 0 | 59 |
| Cotton | 0 | 50 |
| Evening Primrose | 0 | 81 |
| Filbert | 0 | 16 |
| Flax | 58 | 14 |
| Grape | 0 | 71 |
| Hemp | 20 | 60 |
| Hickory | 0 | 17 |
| Candlenut | 29 | 40 |
| Macadamia | 0 | 10 |
| Neem | 1 | 20 |
| Olive | 0 | 8 |
| Palm kernel | 0 | 2 |
| Peanut | 0 | 29 |
| Pistachio | 0 | 19 |
| Pumpkin | 8 | 50 |
| Rice bran | 1 | 35 |
| Safflower | 3 | 75 |
| Sesame | 0 | 45 |
| Soybean | 7 | 50 |
| Sunflower | 0 | 65 |
| Walnut | 6 | 51 |
| Wheat germ | 5 | 50 |

The unsaturated acids or esters thereof typically constitute from about 0.01 wt. % to about 20 wt. %, in some embodiments from about 0.1 wt. % to about 10 wt. %, and in some embodiments, from about 0.5 wt. % to about 5 wt. % of the blood cell barrier composition. Of course, the composition may also contain other ingredients if desired. For instance, the unsaturated aliphatic acid or ester thereof may be used as a primary oxidizing agent in conjunction with a secondary oxidizing agent that enhances the reaction rate of the aliphatic acid. Such a secondary oxidizing agent may include, for example, a stabilized peroxide (e.g., urea peroxide). It is believed that the secondary oxidizing agent helps to accelerate the rate at which cyclic peroxide is formed. As more peroxide develops, the secondary oxidizing agent feeds a self-catalyzing reaction, accelerating the reaction rate and ability to remove red blood cells from a whole blood sample.

It may also be desired to employ a cell lysing agent to facilitate the disruption the membrane of an erythrocyte and thereby boost the ability of the composition to separate the red blood cells. One particularly suitable type of cell lysing agent is a surfactant, such as a nonionic, anionic, cationic, and/or amphoteric surfactant. Suitable nonionic surfactants may include, for instance, alkyl polysaccharides, amine oxides, block copolymers, castor oil ethoxylates, ceto-oleyl alcohol ethoxylates, ceto-stearyl alcohol ethoxylates, decyl alcohol ethoxylates, dinoyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, mono-branched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tallow oil fatty acid ethoxylates, tallow amine ethoxylates, tridecanol ethoxylates, acetylenic diols, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SUR-FYNOL® range of acetylenic diol surfactants available from Air Products and Chemicals of Allentown, Pa.; the TWEEN® range of polyoxyethylene surfactants available from Fisher Scientific of Pittsburgh, Pa.; and the TRITON® range of polyoxyethylene surfactants (e.g., TRITON® X-100, polyoxyethylene-10 isooctylcyclohexyl ether) available from Sigma-Aldrich Chemical Co. of St. Louis, Mo.

Alkyl glycoside nonionic surfactants may also be employed that are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543, which are incorporated herein in their entirety by reference thereto for all purposes, describe alkyl glycosides and/or methods for their preparation. Commercially available examples of suitable alkyl glycosides include Glucopon™ 220, 225, 425, 600 and 625, all of which are available from Cognis Corp. of Cincinnati, Ohio. These products are mixtures of alkyl mono- and oligoglucopyranosides with alkyl groups based on fatty alcohols derived from coconut and/or palm kernel oil. Glucopon™ 220, 225 and 425 are examples of particularly suitable alkyl polyglycosides. Glucopon™ 220 is an alkyl polyglycoside that contains an average of 1.4 glucosyl residues per molecule and a mixture of 8 and 10 carbon alkyl groups (average carbons per alkyl chain-9.1). Glucopon™ 225 is a related alkyl polyglycoside with linear alkyl groups having 8 or 10 carbon atoms (average alkyl chain-9.1 carbon atoms) in the alkyl chain. Glucopon™ 425 includes a mixture of alkyl polyglycosides that individually include an alkyl group with 8, 10, 12, 14 or 16 carbon atoms (average alkyl chain-10.3 carbon atoms). Glucopon™ 600 includes a mixture of alkyl polyglycosides that individually include an alkyl group with 12, 14 or 16 carbon atoms (average alkyl chain 12.8 carbon atoms). Glucopon™ 625 includes a mixture of alkyl polyglycosides that individually include an alkyl group having 12, 14 or 18 carbon atoms (average alkyl chain 12.8 carbon atoms). Still other suitable alkyl glycosides are available from Dow Chemical Co. of Midland, Mich. under the Triton™ designation, e.g., Triton™ CG-110 and BG-10.

Exemplary anionic surfactants include alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkyllauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof. Particular examples of anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group may be straight chain (e.g., lauryl) or branched (e.g., 2-ethylhexyl). The cation of the anionic surfactant may be an alkali metal (e.g., sodium or potassium), ammonium, $C_1$-$C_4$ alkylammonium (e.g., mono-, di-, tri-), or $C_1$-$C_3$ alkanolammonium (e.g., mono-, di-, tri). More specifically, such anionic surfactants may include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Amphoteric surfactants may also be employed, such as derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine. Additional classes of amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Cationic surfactants may also be employed in the present invention, such as alkyl dimethylamines, alkyl amidopropylamines, alkyl imidazoline derivatives, quaternized amine ethoxylates, quaternary ammonium compounds, etc. Still other suitable cell lysing agents for use herein include biguanide and derivatives thereof, organic sulfur compounds, organic nitrogen compounds, phenyl and phenoxy compounds, phenolic compounds, aldehydes (e.g., glutaraldehyde or formaldehyde), glyoxal, parabens (e.g., ethyl paraben, propyl paraben, or methyl paraben), alcohols, such as aliphatic alcohols having from 1 to 16 carbon atoms, and preferably from 1 to 6 (e.g., methanol, ethanol, propanol, isopropanol, butanol, pentanol, octanol) and aromatic alcohols having from 6 to 30 total carbon atoms (e.g., naphtol), and mixtures thereof.

Typically, the cell lysing agent is present in such an amount that the ratio of the unsaturated fatty acid (or ester thereof) to the cell lysing agent is from about 1:1 up to about 30:1, in some embodiments from about 5:1 to about 25:1, and in some embodiments, from about 10:1 or 20:1. For example, the blood cell barrier composition may contain from about 0.001 wt. % to about 5 wt. %, in some embodiments from about 0.01 wt. % to about 2 wt. %, and in some embodiments, from about 0.05 wt. % to about 1 wt. % of unsaturated fatty acids (or esters thereof) by volume of the cell lysing agents.

Besides the ingredients mentioned above, the blood cell barrier composition may also contain one or more additional ingredients to impart a variety of different benefits. For example, the blood cell barrier composition may contain a chelating agent, which is a substance whose molecules can form one or more bonds with a metal ion. In particular, water often contains metal ions, such as calcium ions, that might react with anionic components (e.g., surfactants, acids, etc.) present within the blood cell barrier composition. Without being limited by theory, it is believed that a chelating agent can form a complex with such metal ions so that the remaining components are capable of fulfilling their desired function. Some examples of chelating agents that may be used in the blood cell barrier composition of the present invention include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and so forth.

The blood cell barrier composition may also include various other components as is well known in the art, such as agglutinating agents (e.g., lectin and derivatives thereof), binders, humectants, biocides or biostats, preservatives, electrolytic salts, pH adjusters, etc. For example, various components for use in a blood cell barrier composition are described in U.S. Pat. Nos. 5,681,380 to Nohr, et al. and 6,542,379 to Nohr, et al., which are incorporated herein in their entirety by reference thereto for all purposes. Examples of suitable humectants include, for instance, ethylene glycol; diethylene glycol; glycerin; polyethylene glycol 200, 400, and 600; propane 1,3 diol; propylene-glycolmonomethyl ethers, such as Dowanol PM (Gallade Chemical Inc., Santa Ana, Calif.); polyhydric alcohols; or combinations thereof.

To form the blood cell barrier composition, its components are first typically dissolved or dispersed in a solvent. For example, one or more of the above-mentioned components may be mixed with a solvent, either sequentially or simultaneously, to form a blood cell barrier composition that may be easily applied to a porous membrane. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. The concentration of solvent in the blood cell barrier composition is generally high enough to allow easy application, handling, etc. If the amount of solvent is too large, however, the amount of unsaturated fatty acid (or ester thereof) deposited might be too low to provide the desired separation. Although the actual concentration of solvent employed will generally depend on the nature of the blood cell barrier composition and the membrane to which it is applied, it is nonetheless typically present in an amount from about 40 wt. % to about 99 wt. %, in some embodiments from about 50 wt. % to about 95 wt. %, and in some embodiments, from about 60 wt. % to about 90 wt. % of the blood cell barrier composition (prior to drying).

A variety of techniques may be used for applying the blood cell barrier composition to a porous membrane. For instance, the blood cell barrier composition may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable electronic engraved example for a primary delivery zone is about 200 deposits per lineal inch of surface, or about 40,000 deposits per square inch. By providing such a large number of small deposits, the uniformity of the deposit distribution may be enhanced. Also, because of the large number of small deposits applied to the surface of a membrane, the deposits more readily resolidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used to apply the composition.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with a membrane upon which the composition is to be printed. The blood cell barrier composition is painted onto the screen, and transferred by rubbing the screen (which is in contact with the substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the membrane. Two techniques are generally utilized, i.e., "DOD" (prop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink-jet system varies on the type of material to be printed from the print head. For example, conductive materials are sometimes required for continuous systems because the droplets are deflected electrostatically.

In addition to the printing techniques mentioned above, any other suitable application technique may be used in the present invention. For example, other suitable printing techniques may include, but not limited to, such as laser printing, thermal ribbon printing, piston printing, spray printing, flexographic printing, etc. Still other suitable application techniques may include bar, roll, knife, curtain, spray, slot-die, dip-coating, drop-coating, extrusion, stencil application, striping, etc. Such techniques are well known to those skilled in the art.

Regardless of the method of application, the blood cell barrier composition may sometimes be dried at a certain temperature to drive any solvent therefrom. For example, the membrane may be heated to a temperature of at least about 50° C., in some embodiments at least about 70° C., and in some embodiments, at least about 80° C. By minimizing the amount of solvent in the blood cell barrier composition, a larger amount of unsaturated fatty acid (or ester thereof) may be available for contacting the whole blood sample, thereby enhancing it ability to separate red blood cells. It should be understood, however, that relatively small amounts of solvent may still be present. For example, the dried blood cell barrier composition may contain a solvent in an amount less than about 10% by weight, in some embodiments less than about 5% by weight, and in some embodiments, less than about 1% by weight.

The blood cell barrier composition is generally applied to a porous membrane to form a barrier zone. The barrier zone is positioned upstream from and in fluid communication with the detection zone of the lateral flow device. A first porous membrane, for example, may be provided as a separate material or pad that is positioned adjacent to a second porous membrane, which defines the detection zone. In such embodiments, the separated plasma may flow through the pores of the first porous membrane and then through the pores of the second porous membrane until reaching the detection zone. Alternatively, the barrier zone may be formed on the same membrane as the detection zone. In this manner, the barrier zone of the present invention is integrated within the lateral flow device itself, which provides an efficient, simple, and cost effective method for separating red blood cells from a whole blood sample.

Referring to FIG. 1, for example, one embodiment of the present invention is shown in which a single porous membrane defines both the barrier zone and detection zone. More specifically, a lateral flow device 20 is shown that contains a porous membrane 23 carried by an optional support 21. The porous membrane 23 may be formed from any material as is known in the art. For example, the porous membrane 23 may be formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, glass, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer;

cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The pores of the porous membrane 23 may have an average size of from about 1 micron to about 50 microns, in some embodiments from about 5 microns to about 30 microns, and in some embodiments from about 5 microns to about 15 microns. The size and shape of the porous membrane 23 may also vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

The support 21 may be positioned directly adjacent to the porous membrane 23 as shown in FIG. 1, or one or more intervening layers may be positioned between the porous membrane 23 and the support 21. If desired, the support 21 may be formed from a material that is transmissive to light, such as transparent or optically diffuse (e.g., translucent) materials. Also, it is generally desired that the support 21 is liquid-impermeable so that fluid flowing through the membrane 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the porous membrane 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the porous membrane 23 may be cast onto the support 21, wherein the resulting laminate may be die-cut to the desired size and shape. Alternatively, the porous membrane 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 20 may also contain an absorbent material 28 that is positioned adjacent to the membrane 23. The absorbent material 28 assists in promoting capillary action and fluid flow through the membrane 23. In addition, the absorbent material 28 receives fluid that has migrated through the entire porous membrane 23 and thus draws any unreacted components away from the detection region. Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

Referring again to FIG. 1, the porous membrane 23 defines a barrier zone 35 that is configured to facilitate the separation of red blood cells from the whole blood sample. In this manner, the blood plasma is analyzed at a detection zone 31, which is located downstream from the blood cell barrier zone 35. The barrier zone 35 may provide any number of distinct regions (e.g., lines, dots, etc.). The regions may be disposed in the form of lines in a direction that is substantially perpendicular to the flow of the test sample through the membrane 23. Likewise, in some embodiments, the regions may be disposed in the form of lines in a direction that is substantially parallel to the flow of the test sample through the membrane 23.

To initiate the detection of an analyte, the whole blood sample may be applied (such as with a lancet, needle, dropper, pipette, capillary device, etc.) directly to the barrier zone 35 or to a portion of the porous membrane 23 through which it may then travel in the direction illustrated by arrow "L" in FIG. 1 to reach the barrier zone 35. In one embodiment, a metering channel (not shown) may be formed in the membrane 23, such as described in U.S. Patent Application Publication No. 2006/0246600 to Yang, et al., which is incorporated herein in its entirety by reference thereto for all purposes. In such embodiments, the sample may be applied to the metering channel for subsequent transfer to the barrier zone 35. In still other embodiments, the whole blood sample may first be applied to a separate sample application pad 24 located upstream from the barrier zone 35 and in fluid communication with the porous membrane 23. Regardless of the location at which the sample is applied, a diluent may be employed that helps initiate flow of the sample in the direction of the detection zone 31. For example, upon application, the diluent may flow through the membrane 23 until reaching the sample application zone. The diluent then flows with the whole blood sample and helps carry it to the barrier zone 35 and the detection zone 31. The diluent may be any material having a viscosity that is sufficiently low to allow movement of the fluid by capillary action and that supports a reaction between the analyte and any binding agents (e.g., does not interfere with antibody/antigen interaction). In one embodiment, the diluent contains water, a buffering agent; a salt (e.g., NaCl); a protein stabilizer (e.g., BSA, casein, trehalose, or serum); and/or a detergent (e.g., nonionic surfactant). Representative buffering agents include, for example, phosphate-buffered saline (PBS) (e.g., pH of 7.2), 2-(N-morpholino) ethane sulfonic acid (MES) (e.g., pH of 5.3), HEPES buffer, TBS buffer, etc., and so forth.

The detection mechanism (e.g., biological or non-biological) employed in the lateral flow assay device may vary depending on the analyte of interest. Regardless, the reagents involved in the reaction mechanism are typically diffusively immobilized on the lateral flow device prior to application of the whole blood sample. This provides a variety of benefits, including the elimination of the need for a subsequent user to handle and mix the reagents with the sample or a diluent. In this regard, the reagents may be disposed in a reagent zone located upstream from, downstream from, or at the location where the blood sample is applied. In one embodiment, for example, a reagent zone 22 is employed that is formed from a separate material or pad (e.g., glass fiber pad). Alternatively, the reagent zone may simply be formed on the porous membrane.

Although any reaction mechanism may be employed, one particular embodiment of the present invention relies upon immunospecific reactions between binding pairs (e.g., antibodies and antigens) to detect the analyte in the whole blood sample. Various immunoassay formats may also be used to test for the analyte. In one embodiment, for example, a "sandwich" assay format is utilized in which the analyte has an affinity for the specific binding member of a conjugated probe and a receptive material in the detection zone. The analyte typically has two or more binding sites (e.g., epitopes), one of which becomes occupied by the specific binding member of the conjugated probe. However, the free binding site of the analyte may subsequently bind to the receptive material to form a new ternary sandwich complex. Alternatively, the analyte may be detected using direct or indirect "competitive" assay formats. For example, the specific binding member of the conjugated probe may be the same as or an analog of the analyte. Upon reaching the detection zone, the conjugated detection probe and the analyte thus compete for available binding sites of the receptive material. Similarly, the receptive material in the detection zone may be the same as or an analog of the analyte. The receptive material and the analyte thus compete for available binding sites of the conjugated probe. Of course, any other assay format is also suitable for use in the present invention.

Regardless of the format employed, immunoassays generally employ a substance that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. Nos. 5,670,381 to Jou, et al. and 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

The detectable substance may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. Nos. 5,670,381 to Jou, et al.; 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "Transfluo-Sphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In performing an immunoassay, it is normally desired to modify the detection probes so that they are more readily able to bind to the analyte. For example, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte (i.e., "analog") may be used so long as it has at least one epitope in common with the analyte.

The specific binding members may be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, such as with poly(thiophenol), the detection probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to FIG. 1, a receptive material (not shown) may also be non-diffusively immobilized within the detection zone 31 that is capable of binding to the analyte and/or to the specific binding member of the conjugated detection probes, depending on the assay format employed. The receptive material may be selected from the same materials as the specific binding members described above, including, for instance, antigens; haptens; antibody-binding proteins, such as protein A, protein G, or protein A/G; neutravidin (a deglycosylated avidin derivative), avidin (a highly cationic 66,000-dalton glycoprotein), streptavidin (a nonglycosylated 52,800-dalton protein), or captavidin (a nitrated avidin derivative); primary or secondary antibodies, and derivatives or fragments thereof. In one embodiment, for example, the receptive material is an antibody specific to an antigen within the test sample. The receptive material serves as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized first receptive material. Upon being bound to the immobilized receptive material, the complexed probes form a new ternary sandwich complex.

The detection zone 31 may provide any number of distinct detection regions so that a user may better determine the concentration of one or more analytes within a test sample. Each region may contain the same receptive materials, or may contain different receptive materials. For example, the zone may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20. Further, other than the detection zone 31, the lateral flow device 20 may also define various other zones for enhancing detection accuracy, such as internal calibration zones, control zones, etc. Examples of such additional zones are described in more detail in U.S. Patent Application Publication Nos. 2006/0223193 to Song, et al.; 2006/0246601 to Song, et al.; and 2007/0048807 to Song, which are incorporated herein in their entirety by reference thereto for all purposes.

Qualitative, semi-quantitative, and quantitative results may be obtained in accordance with the present invention. For example, when it is desired to semi-quantitatively or quantitatively detect an analyte, the intensity of any signals produced at the detection zone 31 may be measured with an optical reader. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the intensity of a fluorescence signal. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to signal intensity.

Although various embodiments of device configurations have been described above, it should be understood, that a device of the present invention may generally have any configuration desired, and need not contain all of the components described above. Various other device configurations, for instance, are described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

The present invention may be better understood with reference to the following examples.

Example 1

A circle of Whatman filter paper (Qualitative 18.5 cm) was cut into strips (16 cm×2 cm). A thin line of linoleic acid was placed 8 cm from the bottom end of the strip using a syringe with needle, to lay down a thin line of liquid (approximately 5-10 μl). Next, a drop (20 μl) of fresh human blood was placed onto the strip 4 cm up from the bottom. A control strip was prepared in a similar manner except no linoleic acid was placed on the control strip. The strips were then attached to a glass rod, being 6 cm away from each other, using scotch tape. In a manner similar to paper chromatography, the strips were placed into a tall beaker (2 liter volume) containing deionized water (50 ml) in such a manner that the bottom end of the paper strips just entered the water. The water wicked up the vertically hanging strips. The blood was observed to move up the strips being eluted by the water. On the control strip, the blood was observed to wick up the entire strip over 30 minutes time unhindered, leaving a light trail of red brown color.

For the strip that had the linoleic acid, the blood spot was observed to halt at the line where the linoleic acid had been placed. The system was allowed to run for another 20 minutes after which time the strips were taken out and allowed to air dry. Both strips were then sprayed with a ninhydrin spray to detect amino acids. Both strips visually showed the presence of amino acids by developing a purple color. The control had traces present along the length and a strong presence where the blood spot had stopped. In contrast, on the linoleic acid strip, the red/brown spot had stopped at the linoleic acid line, but the ninhydrin spray visually indicated the presence of amino acids after the line indicating how effectively the linoleic acid had halted the hemoglobin and blood cell membranes (no red/brown trail or spot), but had allowed the other useful biomolecular analytes to pass through undeterred.

Example 2

The experiment described in Example 1 was repeated but using nitrocellulose lateral flow membrane strips (Bangs Laboratories Inc., Fishers Ind.) in place of the paper strips. The same procedure was conducted and at the end of the flow period (20 minutes) the strips were allowed to dry. Similar to the strips in Example 1, the blood spot was halted at the linoleic acid line. In contrast, the control strip allowed the blood to travel up the entire length of the strip. The strips were then sprayed with phenolphthalin solution followed by a 3% solution of hydrogen peroxide in water (a spot test for traces of dried blood and hemoglobin; Ervin Jungreis "Spot test analysis" $2^{nd}$ edition, John Wiley & Sons, Inc. NY 1997). With the control strip, the entire length of the strip gave a visual indication (formation of pink color) for the presence of dried blood and/or hemoglobin with the majority of it being at the finish end of the strip. For the strip with the linoleic acid line, no pink color developed, thereby indicating that there was no blood or hemoglobin beyond the line containing linoleic acid.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A lateral flow device for detecting the presence of an analyte in a whole blood sample, the device comprising a porous membrane, wherein the porous membrane further comprises:
    a barrier zone for separating red blood cells from the whole blood sample, wherein the barrier zone is formed from a blood cell barrier composition that comprises an unsaturated aliphatic fatty acid or ester thereof having a carbon chain of at least $C_8$ and more than one carbon-carbon double bond, wherein the blood cell barrier composition prevents the penetration of red blood cells into the porous membrane; and
    a detection zone for detecting the analyte, the detection zone being located downstream from the barrier zone and in fluid communication therewith, wherein the barrier zone and detection zone are located in the same plane, further wherein the barrier zone is in the form of a first line and the detection zone is in the form of a second line, wherein the first and second lines are spaced apart from each other by a section of the porous membrane.

2. The lateral flow device of claim 1, wherein the unsaturated aliphatic fatty acid or ester thereof has a carbon chain of at least $C_{15}$ and at least two carbon-carbon double bonds.

3. The lateral flow device of claim 1, wherein the blood cell barrier composition includes an omega-3 fatty acid, omega-6 fatty acid, an ester of an omega-3 fatty acid, an ester of an omega-6 fatty acid, or a mixture thereof.

4. The lateral flow device of claim 1, wherein the blood cell barrier composition includes linoleic acid, α-linolenic acid, eicosadienoic acid, eicosatrienoic acid, arachidonic acid, eicosapentaenoic acid, docosahexaenoic acid, an ester thereof, or a mixture thereof.

5. The lateral flow device of claim 1, wherein the blood cell barrier composition includes linoleic acid or an ester thereof.

6. The lateral flow device of claim 1, further comprising detection probes that are capable of generating a detection signal within the detection zone.

7. The lateral flow device of claim 6, wherein a receptive material is immobilized within the detection zone that is capable of binding to the detection probes or conjugates thereof.

8. The lateral flow device of claim 7, wherein the detection probes are conjugated with a specific binding member that preferentially binds to the analyte.

9. A method for detecting the presence of an analyte in a whole blood sample, the method comprising:
    providing a lateral flow device that comprises a porous membrane, wherein the porous membrane further comprises a barrier zone and a detection zone in fluid communication therewith, wherein the barrier zone is formed from a blood cell barrier composition that comprises an unsaturated aliphatic fatty acid or ester thereof having a carbon chain of at least $C_8$ and more than one carbon-carbon double bond, wherein the blood cell barrier composition prevents the penetration of red blood cells into the porous membrane, wherein the barrier zone and detection zone are located in the same plane, and, further wherein the barrier zone is in the form of a first line and the detection zone is in the form of a second line, wherein the first and second lines are spaced apart from each other by a section of the porous membrane;
    contacting the barrier zone with the whole blood sample so that blood plasma, is separated from the sample and flows to the detection zone; and
    detecting the presence of the analyte within the blood plasma at the detection zone.

10. The method of claim 9, wherein the volume of the whole blood sample is less than about 10 microliters.

11. The method of claim 9, wherein the unsaturated aliphatic acid or ester thereof has a carbon chain of at least $C_{15}$ and at least two carbon-carbon double bonds.

12. The method of claim 9, wherein the blood cell barrier composition includes an omega-3 fatty acid, omega-6 fatty acid, an ester of an omega-3 fatty acid, an ester of an omega-6 fatty acid, or a mixture thereof.

13. The method of claim 9, wherein the blood cell barrier composition includes linoleic acid, α-linolenic acid, eicosadienoic acid, eicosatrienoic acid, arachidonic acid, eicosapentaenoic acid, docosahexaenoic acid, an ester thereof, or a mixture thereof.

14. The method of claim 9, wherein the blood cell barrier composition includes linoleic acid or an ester thereof.

15. The method of claim 9, wherein the lateral flow device further comprises detection probes that are capable of generating a detection signal within the detection zone.

16. The method of claim 15, wherein a receptive material is immobilized within the detection zone that is capable of binding to the detection probes or conjugates thereof.

17. The method of claim 15, wherein the detection probes are conjugated with a specific binding member that preferentially binds to the analyte.

18. The method of claim 9, further comprising supplying a diluent to the lateral flow device to facilitate flow of the blood plasma to the detection zone.

19. The lateral flow device of claim 1, wherein the unsaturated fatty acid or ester thereof is capable of undergoing autoxidation in the presence of air and the whole blood sample to release a peroxide.

20. The lateral flow device of claim 19, wherein the released peroxide is capable of inducing the formation of crenated blood cells in the sample.

21. The lateral flow device of claim 20, wherein the crenated blood cells are trapped by the barrier zone before reaching the detection zone.

22. The lateral flow device of claim 1, wherein the device is an in vitro test device.

23. The lateral flow device of claim 1, wherein the first and second lines are disposed in a direction that is substantially perpendicular to the flow of the sample through the device.

* * * * *